(12) United States Patent
Chelyapov (10) Patent No.: US 8,324,357 B2
(45) Date of Patent: Dec. 4, 2012

(54) UNIVERSAL FIELDABLE ASSAY WITH UNASSISTED VISUAL DETECTION

(75) Inventor: Nicolas Chelyapov, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 1607 days.

(21) Appl. No.: 11/682,796

(22) Filed: Mar. 6, 2007

(65) Prior Publication Data

US 2007/0264650 A1    Nov. 15, 2007

Related U.S. Application Data

(60) Provisional application No. 60/779,994, filed on Mar. 6, 2006.

(51) Int. Cl.
*A61K 31/70*    (2006.01)
*C07H 21/04*    (2006.01)

(52) U.S. Cl. .................... 536/23.1; 536/24.5; 514/44

(58) Field of Classification Search ................... None
See application file for complete search history.

(56) References Cited

OTHER PUBLICATIONS

J. Colin Cox, et al., "Automated Selection Of Aptamers Against Protein Targets Translated In Vitro: From Gene To Aptamer", Nucleic Acids Research, (2002) vol. 30, No. 20 *e108*, pp. 1-14.

Razvan Nutiu, et al., "*Structure-Switching Signaling Aptamers: Transducing Molecular Recognition into Fluorescene Signaling*", Chem. Eur. J. (2004) vol. 10, pp. 1868-1876.

Sulay Jhaveri, et al., "In vitro *selection of signaling aptamers*", Nature Biotechnology, (2000), vol. 18, pp. 1293-1297.

Sulay D. Jhaveri and Andrew D. Ellington, "In Vitro *Selection of RNA Aptamers to a Protein Target by Filter Immobilization*", Current Protocols in Nucleic Acid Chemistry (2000) 9.3.1-9.3.25.

Nobuko Hamaguchi, et al., "*Aptamer Beacons for the Direct Detection of Proteins*", Analytical Biochemistry (2001), vol. 294, pp. 126-131.

Sumedha D. Jayasena, "*Aptamers: An Emerging Class of Molecules That Rival Antibodies in Diagnostics*", Clinical Chemistry, (1999) 45:9, pp. 1628-1650.

*Primary Examiner* — Tracy Vivlemore
(74) *Attorney, Agent, or Firm* — DLA Piper LLP (US)

(57) ABSTRACT

A universal detection system based on allosteric aptamers, signal amplification cascade, and eye-detectable phrase transition. A broadly applicable homogeneous detection system is provided. It utilizes components of the blood coagulation cascade in the presence of polystyrene microspheres (MS) as a signal amplifier. Russell's viper venom factor X activator (RVV-X) triggers the cascade, which results in an eye-visible phase transition—precipitation of MS bound to clotted fibrin. An allosteric RNA aptamer, RNA132, with affinity for RVV-X and human vascular endothelial growth factor ($VEGF_{165}$) was created. RNA132 inhibits enzymatic activity of RVV-X. The effector molecule, $VEGF_{165}$, reverses the inhibitory activity of RNA132 on RVV-X and restores its enzymatic activity, thus triggering the cascade and enabling the phase transition. Similar results were obtained for another allosteric aptamer modulated by a protein tyrosine phosphatase. The assay is instrumentation-free for both processing and readout.

16 Claims, 11 Drawing Sheets

(A) Visual presentation of the 96-well plate obtained on a flatbed scanner at the time of 50% reduction in absorbance (T50) for a given concentration of RVV-X (B) Opt

FIGURE 8

Inhibitory effect of RNA37s on the RVV-X-induced phase transition in the BCC-MS detection system

FIGURE 9

The effect of VEGF$_{165}$ on the inhibitory action of RNA132 on RVV-X in RNA132-controlled BCC-MS detection system

SEQUENCE LISTING

```
<160> NUMBER OF SEQ ID NOS: 5

<210> SEQ ID NO 1
<211> LENGTH: 43
<212> TYPE: RNA
<213> ORGANISM: Artificial Sequence
<220> FEATURE:
<223> OTHER INFORMATION: Synthetic oligonucleotide

<400> SEQUENCE: 1
```

-continued

```
gggagcuccu ugagcagucg auuaguuucg acaggaggcu cac                       43

<210> SEQ ID NO 2
<211> LENGTH: 25
<212> TYPE: RNA
<213> ORGANISM: Artificial Sequence
<220> FEATURE:
<223> OTHER INFORMATION: Synthetic oligonucleotde

<400> SEQUENCE: 2
ggaaucagug aaugcuuaua caucc                                           25

<210> SEQ ID NO 3
<211> LENGTH: 68
<212> TYPE: RNA
<213> ORGANISM: Artificial Sequence
<220> FEATURE:
<223> OTHER INFORMATION: Synthetic oligonucleotide

<400> SEQUENCE: 3
gggagggaau cagugaaugc uuauacaucc cuccuugagc agucgauuag uuucgacagg      60
aggcucac                                                              68

<210> SEQ ID NO 4
<211> LENGTH: 68
<212> TYPE: RNA
<213> ORGANISM: Artificial Sequence
<220> FEATURE:
<223> OTHER INFORMATION: Synthetic oligonucleotde

<400> SEQUENCE: 4
gggagggaau cagugaaugc uuauacaucc cuccuugagc agucgauuag uuucgacagg      60
aggcucac                                                              68

<210> SEQ ID NO 5
<211> LENGTH: 80
<212> TYPE: RNA
<213> ORGANISM: Artificial Sequence
<220> FEATURE:
<223> OTHER INFORMATION: Synthetic oligonucleotide

<400> SEQUENCE: 5
gggagucagg gagcgaggac cagacgacgu accuaacccu aacuccuuga gcagucgauu      60
aguuucgaca ggaggcucac                                                 80
```

UNIVERSAL FIELDABLE ASSAY WITH UNASSISTED VISUAL DETECTION

CROSS-REFERENCE TO RELATED APPLICATIONS

The present application claims priority to U.S. Provisional Patent Application Ser. No. 60/779,994, filed on Mar. 6, 2006.

FUNDING

This invention was made with support in part by grants from the National Science Foundation (CCF-0323749), the Defense Advanced Research Projects Agency—Office of Naval Research (DARPA-ONR; N00014-98-1-0664), and the United States National Aeronautics and Space Administration (NASA; NCC2-1224). Therefore, the U.S. government has certain rights.

FIELD OF THE INVENTION

The present invention relates in general to aptamers. More specifically, the invention provides a universal detection system based on allosteric aptamers, signal amplification cascade, and eye-detectable phrase transition.

BACKGROUND OF THE INVENTION

Detecting specific molecules is a crucial task for medicine, biotechnology, chemical and biodefense, and environmental protection. Many new detection systems are developed every year with increasing specificity and sensitivity. These systems include the latest developments in biotechnology and nanotechnology. All of them have one common feature: they employ sophisticated and expensive equipment for the processing and/or the readout of the results.

SUMMARY OF THE INVENTION

A broadly applicable homogeneous detection system has been developed. It utilizes components of the blood coagulation cascade in the presence of polystyrene microspheres (MS) as a signal amplifier. Russell's viper venom factor X activator (RVV-X) triggers the cascade, which results in an eye-visible phase transition—precipitation of MS bound to clotted fibrin. An allosteric RNA aptamer, RNA132, with affinity for RVV-X and human vascular endothelial growth factor (VEGF$_{165}$) was created. RNA132 inhibits enzymatic activity of RVV-X. The effector molecule, VEGF$_{165}$, reverses the inhibitory activity of RNA132 on RVV-X and restores its enzymatic activity, thus triggering the cascade and enabling the phase transition. As few as five femtomoles of VEGF$_{165}$ could be detected by the naked eye within an hour. Similar results were obtained for another allosteric aptamer modulated by a protein tyrosine phosphatase. The assay is instrumentation-free for both processing and readout and can be modified to detect molecules to which aptamers can be obtained.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

BRIEF DESCRIPTION OF THE FIGURES

T(50) is the time for a 50% decrease in OD$_{405}$.

FIG. 10. The effect of VEGF$_{165}$ on the inhibitory action of RNA132 on RVV-X in RNA132-controlled BCC-MS detection system. In the RNA132-controled BCC-MS experiment, VEGF$_{165}$ reversed inhibitory action of RNA132 on the RVV-X-triggered phase transition in a concentration-dependent mode. This effect implies competition between VEGF$_{165}$ and RVV-X for binding to RNA132. Dynamic range of the detection system appeared to be narrow, i.e. about 10-fold range of VEGF$_{165}$ concentrations (6-60 fmol/reaction mix), which is typical for BCC-based assays. The above sensitivity of the assay is within the lower half of the linear range of the VEGF$_{165}$ concentrations detected by ELISA assays commercially available from, e.g., R&D Systems or Cell Sciences. But components of the BCC-MS detection system presented here allow adjusting their relative concentrations to detect the molecule of interest within a wider range of concentrations. The formula to calculate relative effect of different concentrations of VEGF165 is as follows:

$$(T(50)^{+RNA132/-VEGF165} - T(50)^{+RNA132/+VEGF165}) / (T(50)^{+RNA132/-VEGF165} - T(50)^{-RNA132/+VEGF165})$$

Human $VEGF_{165}$, Murine $VEGF_{165}$ and Zebrafish $VEGF_{165}$ have both the same biological function and contain 165 of amino acids. Murine $VEGF_{165}$ has an 89% homology with Human $VEGF_{165}$ where 147 of 165 amino acids are identical. Zebrafish $VEGF_{165}$ has about a 62% amino acid sequence identity with Human $VEGF_{165}$. Human $VEGF_{121}$ is a truncated version of Human $VEGF_{165}$, with 44 amino acids truncated downstream from position 110 of the polypeptide chain. Thus cysteine 137 of $VEGF_{165}$ that forms a photo-inducible cross-link to a uridine at position 14 of RNA VTt44 (which corresponds to position 13 of RNA VTt44(-2) and position 18 of RNA132) is missing in $VEGF_{121}$. Human VEGF/P/GF heterodimer is a protein artificially dimerized in vitro. It consists of Human $VEGF_{165}$ and Placental growth factor. Endocrine gland VEGF is a protein of irrelevant amino acid sequence consisting of 86 amino acids.

DETAILED DESCRIPTION OF THE INVENTION

Aptamers play an increasingly important role in biotechnology and nanotechnology. They can acquire allosteric properties similar to enzymes. There is no established terminology in the field, and these aptamers are variously called allosteric, ligandregulated, ligand-dependent, structure-switching signaling, or modular. Armed with fluorophores, these aptamers can be used for detecting 'effector' molecules, where the readout is performed using the spectrofluorometer. In order to free the readout procedure from any kind of instrumentation, an approach utilizing biochemical amplification is explored.

The biochemical amplification, resulting in an eye-detectable phase transition, is accomplished using the components (Factors X, Va, Prothrombin, and Fibrinogen) of the blood coagulation cascade (BCC). When a specific metalloproteinase, the Russell's viper venom factor X activator (RVV-X), is added to the components of BCC, the cascade is triggered. Triggering of BCC in the context of polystyrene microspheres (MS) results in the eye-detectable clot formation (precipitate of MS bound to fibrin). An RNA aptamer (RNA37s) was SELEXed to RVV-X. When RVV-X is mixed with RNA37s, and the resulting product is added to the components of BCC, clot formation is delayed.

The fusing of RNA37s to another aptamer (RNAVTt44), which binds to human Vascular Endothelial Growth Factor ($VEGF_{165}$), produced a fusion-aptamer RNA132. When RVV-X is mixed with RNA132 and the resulting product is added to the components of BCC, clot formation is also delayed. However, when RVV-X is mixed with RNA132 and then $VEGF_{165}$ is added, the resulting product does not delay clot formation when added to the components of BCC. Hence RNA132 is an allosteric aptamer. The sensitivity of the above assay for $VEGF_{165}$ is essentially the same as the sensitivity of commercially available ELISA. Similar results were obtained for another allosteric aptamer (RNA37sN71 (SEQ ID NO:5)) that was created by fusion of RNA37s with an aptamer for a protein tyrosine phosphatase from *Yersinia enterocolitica*. Presumably this method can be used to create detection systems for other molecules to which aptamers can be selected.

Advantages of the above detection system include: only two pipetting cycles (compared with approximately 10 in ELISA), no washes, no reagents immobilized on solid support, and visual readout without any instrumentation.

SELEX

An RNA aptamer binding to RVV-X was obtained via standard SELEX protocol. The progress of the selection was monitored by determining the dissociation constant of the RNA-protein complex ($K_d$) and by determining how much RNA binds to a single "high" concentration (50 nM) of the protein target in a single point binding assay. Initial pool of unselected RNA (RNA0) had a $K_d$ value of 550±30 nM with the binding of 6.3% in a single point binding assay when the IC binding buffer was used for washing and 2.2% when IC binding buffer+300 mM NaCl (high salt) was used for washing, with 1.2% background noise. After five rounds of selection, $K_d$ for RNA5 dropped to 22±3.0 nM; binding in a single point binding assay increased to 23% and 7% respectively. An attempt to clone and sequence at this point failed to produce a consensual sequence of reasonable length. After the ninth round of selection, $K_d$ for RNA9 went down to 2.2±0.9 nM, and the results for the single point binding assay were 55% and 43% respectively, with 2% background noise. A consensual sequence for RNA9c was derived from the analysis of 45 clones.

The full length RNA9c (87 bases) containing a consensual 40-mer sequence flanked by the primers showed inhibitory activity of 43% in the RVV-X-SPZXa test. A systematic deletion mutagenesis applied to RNA9c allowed to isolate 43-mer RNA37s. RNA37s showed 84% inhibitory activity in the RVV-XSPZXa test. It also showed concentration-dependent inhibitory effect on the RVV-X-induced clot formation in the BCC-MS detection system.

An aptamer binding to $VEGF_{165}$, RNA VTt44, with one base snipped from both 5'- and 3'-ends (VTt44(-2), was inserted into RNA37s five bases downstream from its 5'-end to create an allosteric aptamer RNA132. This structure appeared to be more stable with ΔG=-24.0 kcal/mol, compared with the "head to tail" version, when RNA37s was directly linked with the 3'-end of RNA VTt44(-2), ΔG=-18.0 kcal/mol (28-30). It is important to note that the putative RNA binding domains for both proteins stayed unhampered in the chimeric RNA132. A possible conformation including pseudoknots was also predicted with ΔG=-27.0 kcal/mol.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

This invention presents an approach for a broadly applicable detection system without using any instrumentation for both processing and readout.

In the last several years aptamers have become widely used as sensors and diagnostic agents with a high level of specificity and sensitivity (1-10). Among other advantages, aptamers can be used in homogeneous assays, thus eliminating reagent immobilization and reducing processing time and manipulation steps (4, 10). Aptamers can acquire allosteric properties similar to enzymes (8, 11-16), and therefore they can be used for detecting 'effector' molecules (8, 15). To achieve the level of sensitivity that rivals more conventional immunoassays (1, 2, 15), aptamer-based detection systems also have to use sensitive and sophisticated instrumentation for processing and readout. In order to free the readout and the processing procedure from any kind of instrumentation, an approach is explored based on allosteric aptamers controlling the biochemical amplification cascade. The biochemical amplification cascade is based on the components of the blood coagulation cascade ($BCC_1$) in the presence of polystyrene microspheres (MS). BCC-MS amplification cascade, results in an eye-visible phase transition, i.e. the precipitation of MS bound to the clotted fibrin. Controlled by an allosteric aptamer, BCC-MS amplification cascade becomes BCC-MS detection system.

Experimental Procedures

Materials. All plasticware including 96-well plates (flat bottom) used in this study were non-stick or low binding from Ambion and Corning. RNase-free water was from Ambion. Reagents for the human blood coagulation cascade: Fibrinogen, Prothrombin, Factor Va, Factor X and also snake venom protease RVV-X and phospholipid vesicles (PCPS) were purchased from Haematologic Technologies. SPECTROZYME®fXa (SPZXa) was from American Diagnostica. PCR and RT-PCR reagents and T7 RNA Polymerase kits were from Promega and Epicentre. Human $VEGF_{165}$, human $VEGF_{121}$, murine $VEGF_{165}$, zebrafish $VEGF_{165}$, endocrine gland VEGF, and human VEGF/PlGF heterodimer were from R&D Systems and USB. Polystyrene microspheres were from Bangs Laboratories. Ready-made polyacrylamide gels were from Invitrogen. Oligonucleotides were synthesized and purified by IDT or Qiagen.

All reactions took place in 50 mM imidazole-HCl, 3 mM $CaCl_2$ buffer, pH 7.8, (IC buffer). Snapshots of the 96-well plates were taken by a Memorex flatbed scanner, model 6142u. BCC-MS Amplification Cascade. A typical reaction mix contained 600 nM PCPS, 230 nM Fibrinogen, 170 nM Prothrombin, 870 fM Factor Va, 580 pM Factor X and 1/450-1/350 dilution of polystyrene microspheres (10% solids) 0.77-1.0 µm in diameter in IC buffer. One hundred microliters of the reaction mix were dispensed into wells of a 96-well plate to which 5-10 µL of a test solution, e.g. RVV-X, were added. After that the plate was immediately placed into a microplate reader (Genios, Tecan) and shaken for 10-30 seconds prior to $OD_{405}$ measurements at 5-10 minute intervals. The relative effect (zero meaning no effect, and one meaning maximal effect) of $VEGF_{165}$ on the inhibition of the phase transition by RNA132 was calculated according to the formula, which allowed graphic presentation for the dynamic range of the reaction:

$$(t_{1/2}^{+RNA132/-VEGF165} - t_{1/2}^{+RNA132/+VEGF165})/(t_{1/2}^{+RNA132/-VEGF165} - t_{1/2}^{-RNA132/+VEGF165}),$$

where $t_{1/2}$ is the time for a 50% reduction in absorbance. The same formula was applied for the calculation of the relative effect for PTPase.

The BCC-MS reaction can be "frozen" at any stage by adding EDTA to 10 mM final concentration.

SELEX Protocol and the Creation of Allosteric Aptamers. Sequences for the initial DNA template library (40N) and primers for the SELEX for aptamer to RVV-X were taken from (17). Large-scale PCR amplification and all other subsequent synthetic and selection steps were performed as described in (17-19) without modification. The initial selection involved 500 picomoles of random RNA library ($3 \times 10^{14}$ molecules). After each round of selection RNA was tested in a nitrocellulose filter binding assay to determine the dissociation constant of aptamer-protein complexes ($K_d$) (19) and in a single point binding assay with equimolar concentrations of protein and RNA (50 nM) (20). In the latter experiments one set of filters was washed with IC buffer. Another set of filters was washed with IC buffer+300 mM NaCl (high salt buffer) to remove more of non-specifically bound RNA. After the fifth and ninth round of selection, RNA was reverse transcribed, DNA was amplified by PCR and cloned. Each time 45 clones were sequenced to determine the presence of consensus sequences. Cloning and sequencing were performed by Laragen.

Three $VEGF_{165}$-binding RNA aptamers, 12t, 84t and 100t described in (21), and three other $VEGF_{165}$-binding RNA aptamers, VPt2, VPt22 and VTt44 described in (22), were synthesized using unmodified NTPs and tested in a gel-shift assay with $VEGF_{165}$. Aptamer VTt44 showed the highest affinity for $VEGF_{165}$ in the IC buffer, since it was initially selected in the presence of calcium, which was absolutely required for high affinity binding of this aptamer to $VEGF_{165}$ (22). Please note that Ca ions are essential for BCC-MS amplification cascade.

Allosteric aptamers were created either by directly fusing of the 5'-end of RNA37s with the 3'-end of an effector aptamer or by inserting an effector aptamer RNA a number of bases downstream into the RNA37s.

RVV-X Activity Determination with SPECTROZYME®fXa (RVV-X-SPZXa Assay). SPECTROZYME®fXa is a chromogenic substrate for the activated Factor X. RVV-X by itself (10 µL, 1.7 nM) or pretreated with aptamers (17 nM) was incubated with Factor X (170 nM) and mixed with 140 µL of SPECTROZYME®fXa (5 mM, IC buffer). Appearance of the chromophore, p-nitroanilide acetate, was monitored over time at 405 nm in a microplate reader. The final measurement was taken 10 minutes after the onset of the reaction. The inhibitory effect of an aptamer on the RVV-X activity was calculated according to the formula:

$$[1-(A^{RVV-X+RNA}-A^{RNA})/(A^{RVV-X}-A^{RNA})]\cdot 100\%.$$

RNA Folding and Minimum Free Energy Calculations. Predictions of the RNA folding patterns with or without pseudoknots and calculations of minimum free energy (ΔG) were done according to algorithms and software presented in (23, 24). Visual representation of the RNA secondary structure based on the above predictions was done using Pseudo-Viewer2 software (25).

DNA Competition Assay for Mapping of RNA132 Binding Sites for RVV-X and $VEGF_{165}$. DNA molecules complementary to various segments of RNA132 were synthesized (see the list in Table 1) and used as competitors to RVV-X and $VEGF_{165}$ in binding to $^{32}$P-labeled RNA132. The complexes were analyzed in a gel-shift assay utilizing 6% PAGE (0.5× TBE). RNA132 (100 fmol) was annealed with DNA (200 fmol) by incubating the mix at 70° for 1 minute with slow cooling to room temperature. Proteins were added to the complex at room temperature and after 15 minutes of incubation the samples were subjected to PAGE. Volumes for bands, determined by Phosphorimager "Storm" (Molecular Dynamics), corresponding to RNA132 complexes with RVV-X or $VEGF_{165}$, with no competing DNA added, were taken as 100% binding. When a full-length DNA complement (DNA I) was competing with the proteins for binding to RNA132, no bands corresponding to the RNA-protein complexes were detected for either of the proteins, thus binding for them was 0%. In a control experiment proteins were annealed with the DNA used at tenfold higher concentrations. No binding was detected between competing DNA and the proteins.

TABLE 1

Mapping of RNA132 binding sites for RVV-X
and VEGF165 in a DNA competition assay.

| DNA | Base position number | Percent binding RVV-X | VEGF$_{165}$ |
|---|---|---|---|
| None added | N/A | 100 | 100 |
| I | 1-68 | 0 | 0 |
| II | 31-68 | 10 | 48 |
| III | 36-68 | 17 | 64 |
| IV | 1-30 | 19 | 14 |
| V | 6-30 | 28 | 36 |
| VI | 8-28 | 51 | 42 |

Results

Homogeneous BCC-MS Amplification Cascade. A biochemical signal amplification cascade, utilizing components of the BCC cascade in the presence of MS was described as a part of a heterogeneous ELISA assay (26). The BCC portion of the amplification cascade consisted of Factors X, Va, II (Prothrombin), and I (Fibrinogen). BCC was triggered by a specific metalloproteinase, the Russell's viper venom factor X activator (RVV-X) (27). RVV-X-initiated BCC resulted in an eye-visible phase transition, i.e. precipitation of MS bound to the clotted fibrin. The assay showed sensitivity of 10-100 fg/ml for RVV-X, which corresponds to 10-100 zeptomoles of the protein detected in 100 μL of a test solution in 60 minutes. The disadvantages of the above assay include its basis on a standard solid support ELISA format that requires multiple washes and reagent transfers. Furthermore, the above assay relies on several specific, not readily available reagents, one of which is a monoclonal antibody conjugated to RVV-X (26).

This invention provides an effective approach overcoming these issues. An allosteric aptamer would substitute for antibodies and conjugates, and would render the assay homogeneous, eliminating washing and minimizing reagent transfer steps. An allosteric aptamer will bind to RVV-X and inhibit its enzymatic activity, while subsequent binding of an effector molecule to the aptamer will modulate the inhibitory effect by reversing it. Thus, an on/off switch for the RVV-X activity will be created depending on the presence of an effector molecule. The allosteric aptamer-controlled detection system based on BCC in the presence of MS (BCC-MS) will require only one variable component—a part of the allosteric aptamer specific to the effector molecule.

Figure 1:
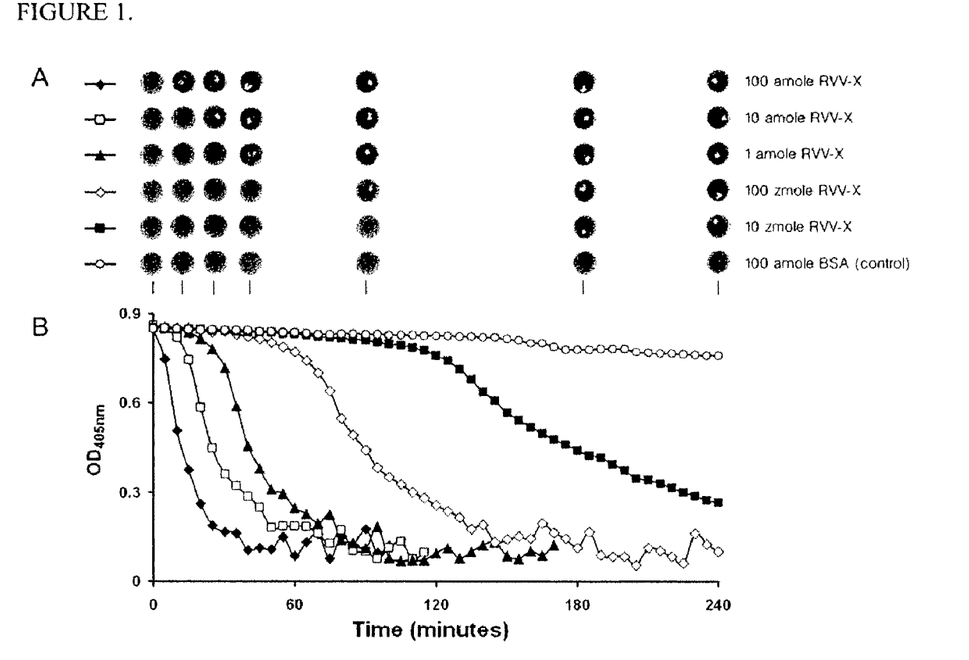
FIG. 1. Kinetics of the phase transition (precipitation of MS bound to the clotted fibrin) in the BCC-MS amplification cascade triggered by the different concentrations of RVV-X. (A) Visual presentation of the 96-well plate obtained on a flatbed scanner at the time of 50% reduction in absorbance ($t_{1/2}$) for a given concentration of RVV-X. (B) Optical density at 405 nm measured on a microplate reader in the same wells at 5-minute intervals.

Components for the homogeneous BCC-MS amplification cascade were derived from (26, 28). Modifications included substitution of the Factor V with the Factor Va, and substitution of the rabbit brain cephalin with the commercially available phospholipid vesicles. FIG. 1 shows the kinetics of the phase transition (clot formation) caused by the RVV-X activity in the BCC-MS amplification cascade monitored both visually and spectrophotometrically at 405 nm. Snapshots of the wells taken at the time of 50% reduction in absorbance ($t_{1/2}$) for different RVV-X concentrations show distinct differences among the wells depending on the progress of the phase transition (FIG. 1A). At the beginning (time zero) all wells have a uniformly whitish, milky appearance, as the MS are in suspension. The well with no RVV-X added (open circles) remains the same during the entire course of the experiment. After 12 minutes, corresponding to $t_{1/2}$ for 100 attomoles of RVV-X (solid diamonds), less opaque material is seen in the corresponding well. No changes are observed in the other wells at this time. At 26 minutes, corresponding to $t_{1/2}$ for 10 attomoles of RVV-X (open squares), less opaque material is seen in the well, as was at 12 minutes for the well with 100 attomoles of RVV-X. The MS in the well with the 100 attomoles of RVV-X are coagulated by this time, and the well has a clear black background. This coagulation pattern is repeated in subsequent wells. Thus, the homogeneous BCC-MS amplification cascade is adequate for the detection of small quantities of RVV-X by the naked eye.

Selection of an Aptamer to RVV-X. An RNA aptamer binding to RVV-X was obtained via standard SELEX protocol (17-19). The progress of the selection was monitored by determining the dissociation constant of the RNA-protein complex ($K_d$) and by determining the fraction of RNA that binds to the target protein at a the same "high" concentration (50 nM) of both the aptamer and the target protein in a single point binding assay. The latter assay was performed using both the binding buffer and the high salt buffer (binding buffer+300 nM NaCl) to decrease the input of nonspecifically bound complexes (20). The initial pool of unselected RNA (RNA0) had a $K_d$ value of 550±23 nM. In a single point binding assay, 6.3% of RNA0 preincubated with RVV-X was bound to the filter when the binding buffer was used for washing, and 2.2% of the RNA0 stayed bound to the filter when the high salt buffer was used for washing, with 1.2% of background noise. After the ninth round of selection, $K_d$ for RNA9 decreased to 2.2±1.9 nM, and the results for the single point binding assay were 55% and 43% respectively, with 2% background noise. A consensus sequence (RNA9c) was derived from the analysis of 45 clones of RT-PCRed RNA9.

The full length RNA9c (87 bases) containing the consensus 40-mer sequence flanked by the primers showed a 43% inhibitory effect on the RVV-X enzymatic activity in the RVV-X-SPZXa assay. A systematic deletion mutagenesis applied to RNA9c enabled the isolation of a minimal 43-mer RNA37s (FIG. 2A) with 84% inhibitory effect on RVV-X in the RVV-X-SPZXa assay. RNA37s also showed a concentration-dependent inhibitory effect on the RVV-X-induced clot formation in the BCC-MS detection system (FIG. 3A). Binding of RNA37s to RVV-X was confirmed in a gel-shift experiment (FIG. 4).

Allosterizing of the Aptamer to RVV-X Human VEGF$_{165}$ was chosen as an effector molecule for the construction of an allosteric aptamer. The choice of VEGF$_{165}$ was based on several criteria, including the availability of high affinity aptamers to VEGF$_{165}$ (21, 22), one of which was shown to be an efficient anti-VEGF$_{165}$ agent in vivo (29). Also there are several natural analogs of the human VEGF$_{165}$ that can be adequate controls for the specificity of the detection system; and there are commercially available highly sensitive ELISA assays for this protein that can serve as reference standards.

Figure 2:
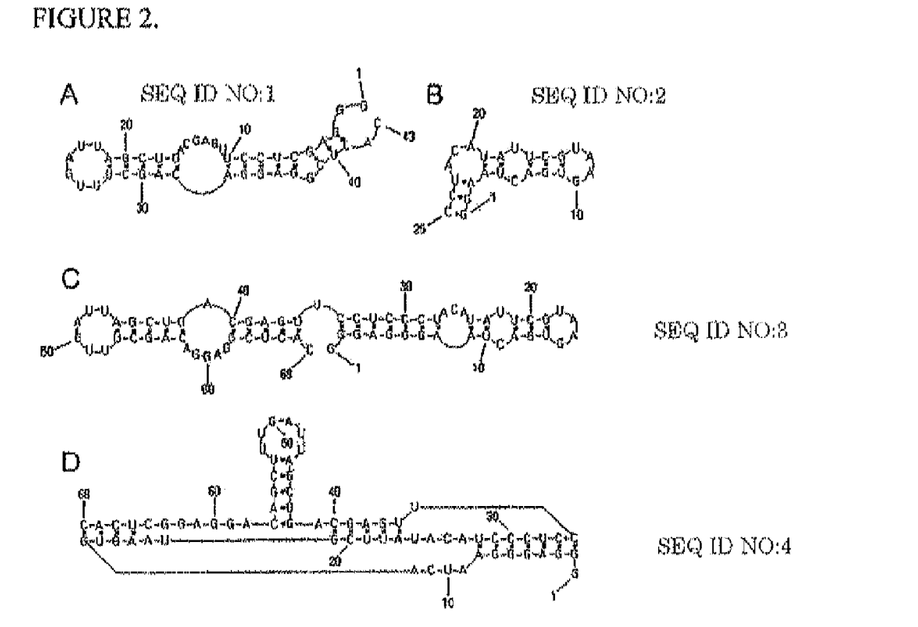
FIG. 2. Schematic representation of the secondary structure folding for the RNA aptamers. (A) RNA37s (SEQ ID NO:1). (B) VTt44(−2) (SEQ ID NO:2). (C) RNA132 without pseudoknots (SEQ ID NO:3). (D) RNA132 with pseudoknots (SEQ ID NO:4).
Figure 3:
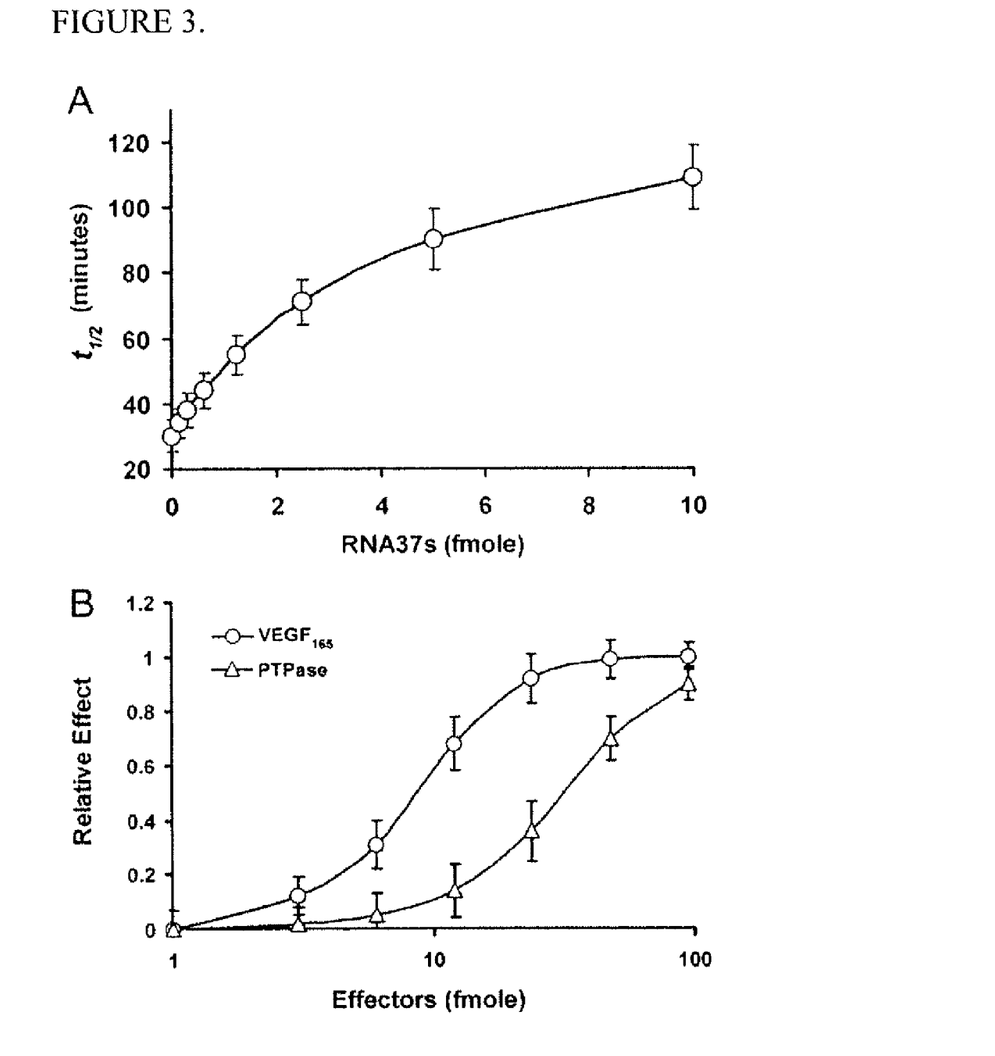
FIG. 3. Kinetics of the phase transition in the BCC-MS detection system. (A) In the presence of different concentrations of RNA37s. (B) The reversal of the inhibitory effect of RNA132 on the phase transition by different concentrations of Human VEGF$_{165}$ and PTPase. The relative effect was calculated according to the formula in the Experimental Procedures section.

An aptamer binding to VEGF$_{165}$, RNA ligand VTt44 (22), with one base omitted from both 5'- and 3'-ends, VTt44(-2), (FIG. 2B), was inserted into RNA37s five bases downstream from its 5'-end to create the allosteric aptamer RNA132 (FIG. 2C). This structure appeared to be more stable when compared with the "head to tail" version, where the 5'-end of RNA37s was directly fused with the 3'-end of VTt44(-2) ($\Delta G=-24.0$ kcal/mol versus $\Delta G=-18.0$ kcal/mol) (23, 24). Presumably, putative RNA binding domains stayed accessible for both proteins in the chimeric RNA132. A possible conformation including pseudoknots was also predicted for RNA132 with $\Delta G=-27.0$ kcal/mol (FIG. 2D) (23).

Figure 4:
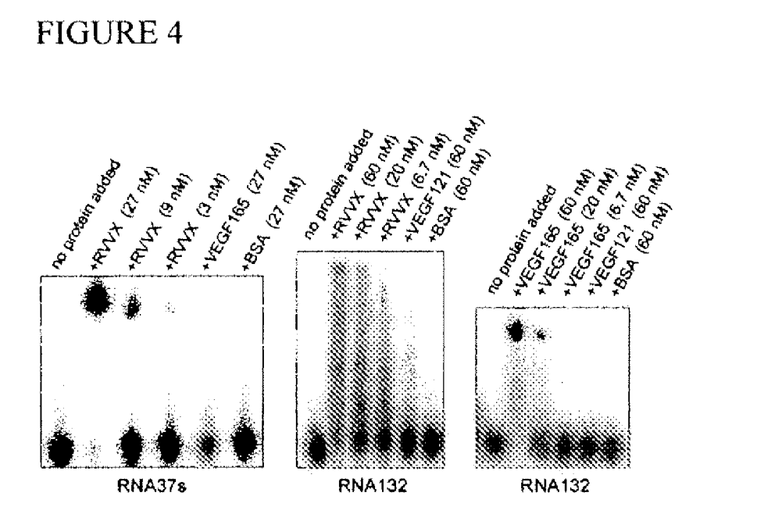
FIG. 4. Gel-shift analysis of RVV-X and Human VEGF$_{165}$ binding to RNA37s and RNA132.

In a gel-shift assay, RVV-X and VEGF$_{165}$ were shown to bind to RNA132 at about equal concentrations (FIG. 4). The dissociation constants for both proteins, 5.7±2.9 nM, appeared to be identical within experimental error. RNA132 was also tested in the RVV-X-SPZXa assay and showed 86% inhibitory effect similar to the effect of RNA37s within experimental error. As tested in the BCC-MS detection system, concentration-dependent inhibitory effect of RNA132 on the phase transition was also similar to RNA37s within experimental error.

The Effector Molecule, $VEGF_{165}$, Reverses Inhibition of the Phase Transition Caused by RNA132. As was shown in the RNA132-controled BCC-MS detection system, $VEGF_{165}$ reversed the inhibitory effect of RNA132 on the RVV-X-triggered phase transition in a concentration-dependent mode (FIG. 3B). This effect suggests a competition between $VEGF_{165}$ and RVV-X for binding to RNA132. Dynamic range for the effect of $VEGF_{165}$ on the reversal of the phase transition in the RNA132-controled BCC-MS detection system appeared to be narrow, i.e. about 10-fold range of $VEGF_{165}$ concentrations (3-30 fmol). This was shown to be typical for the BCC-based detection systems (28). The sensitivity of the detection of $VEGF_{165}$ in the RNA132-controled BCC-MS detection system is within the lower half of the linear range for the $VEGF_{165}$ concentrations detected by commercial ELISA assays.

Another allosteric aptamer (RNA37sN71) modulated by a different effector molecule was created by fusing RNA37s with an aptamer to a protein tyrosine phosphatase (PTPase) from *Yersinia enterocolitica*, N71 (30). In the RNA37sN71-controled BCC-MS detection system, the PTPase also reversed the inhibitory effect of RNA37sN71on the RVV-X-triggered phase transition in a concentration-dependent mode (FIG. 3B), though the curve describing the relative effect of the PTPase was shifted to higher concentrations of PTPase as compared with $VEGF_{165}$.

Figure 5:
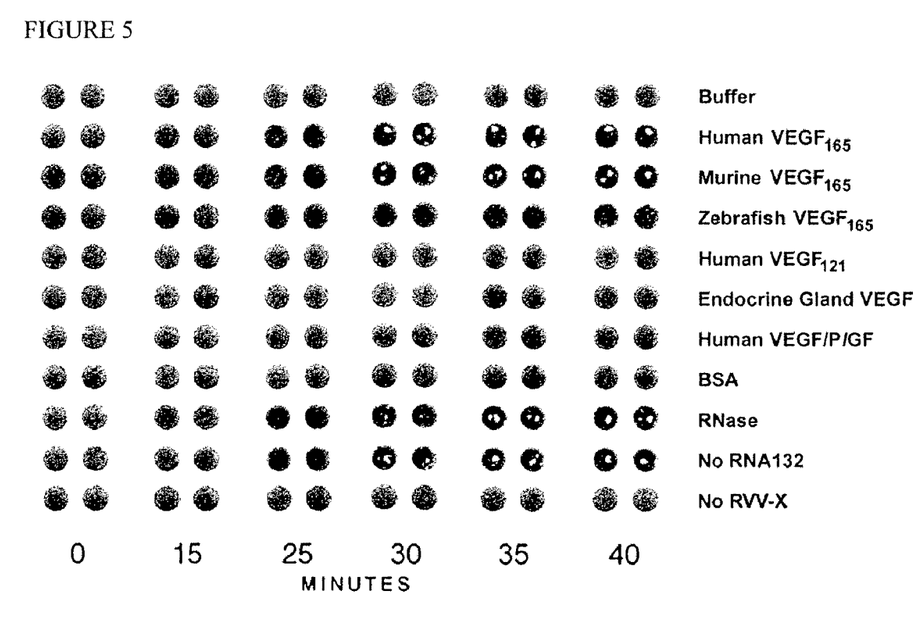
FIG. 5. Visual presentation of the kinetics of clot formation in the RNA132-controled BCC-MS detection system in the presence of 10 fmole of different proteins, except for 100 amole of RNase. Proteins were incubated with a mix of RVV-X and RNA132 for 15 minutes at room temperature in 5-10 µL of IC buffer, followed by the addition of the components of the BCC-MS detection system. At the indicated time points, wells of the 96-well plate were scanned on a flatbed scanner. The results are presented in duplicates.
Figure 6:
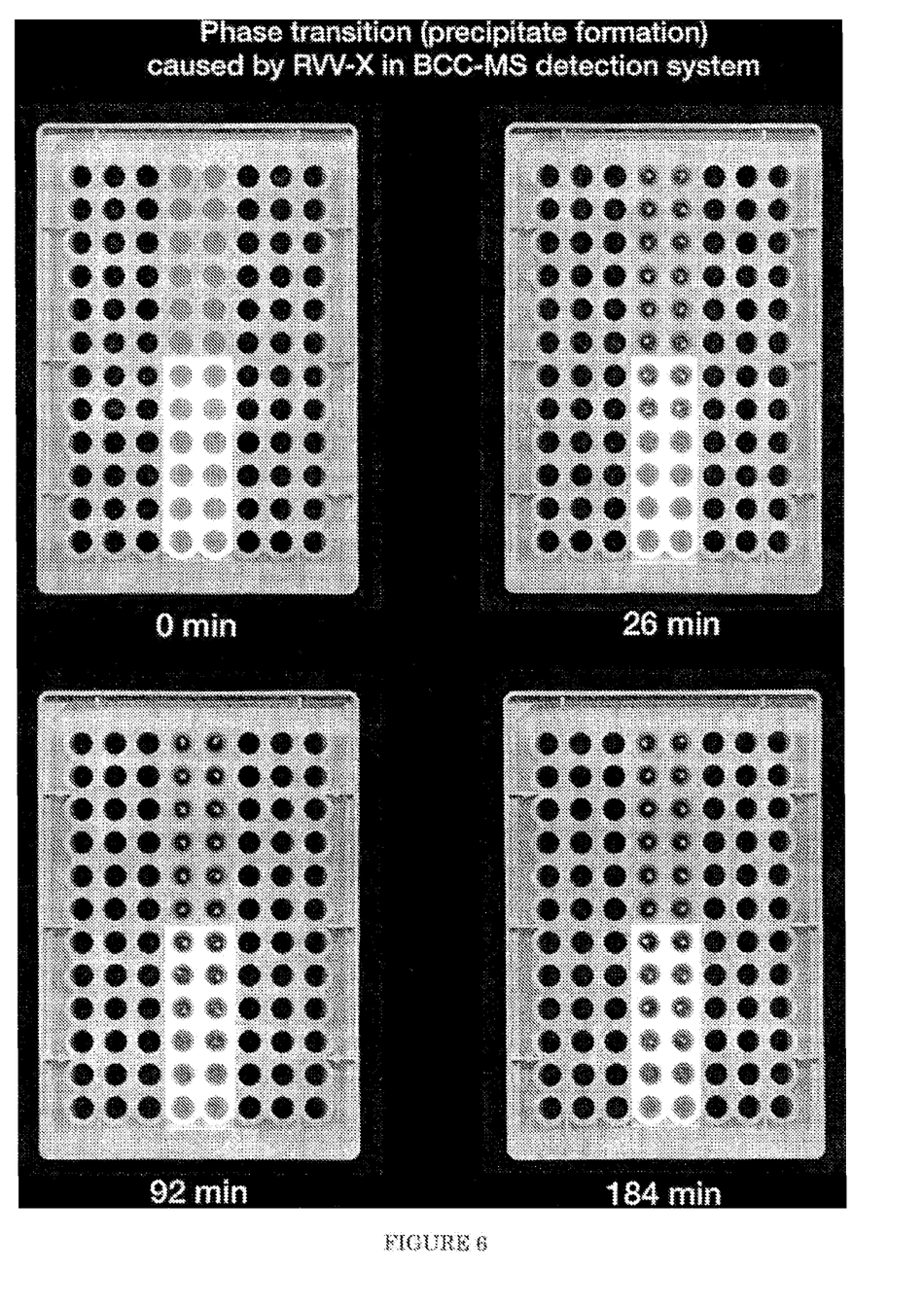
FIG. 6. Phase transition (precipitate formation) caused by RVV-X in BCC-MS detection system.
Figure 7:
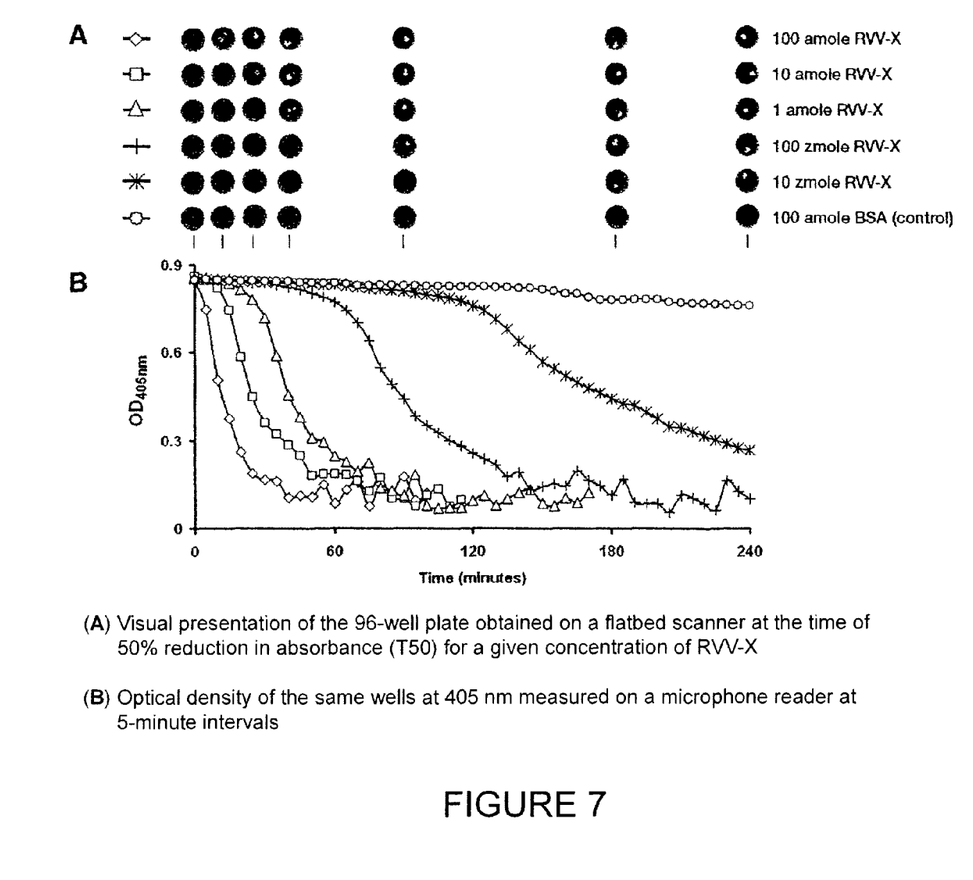
FIG. 7. Kinetics of phase transition (precipitate formation) caused by RVV-X in BCC-MS detection system.
Figure 8:
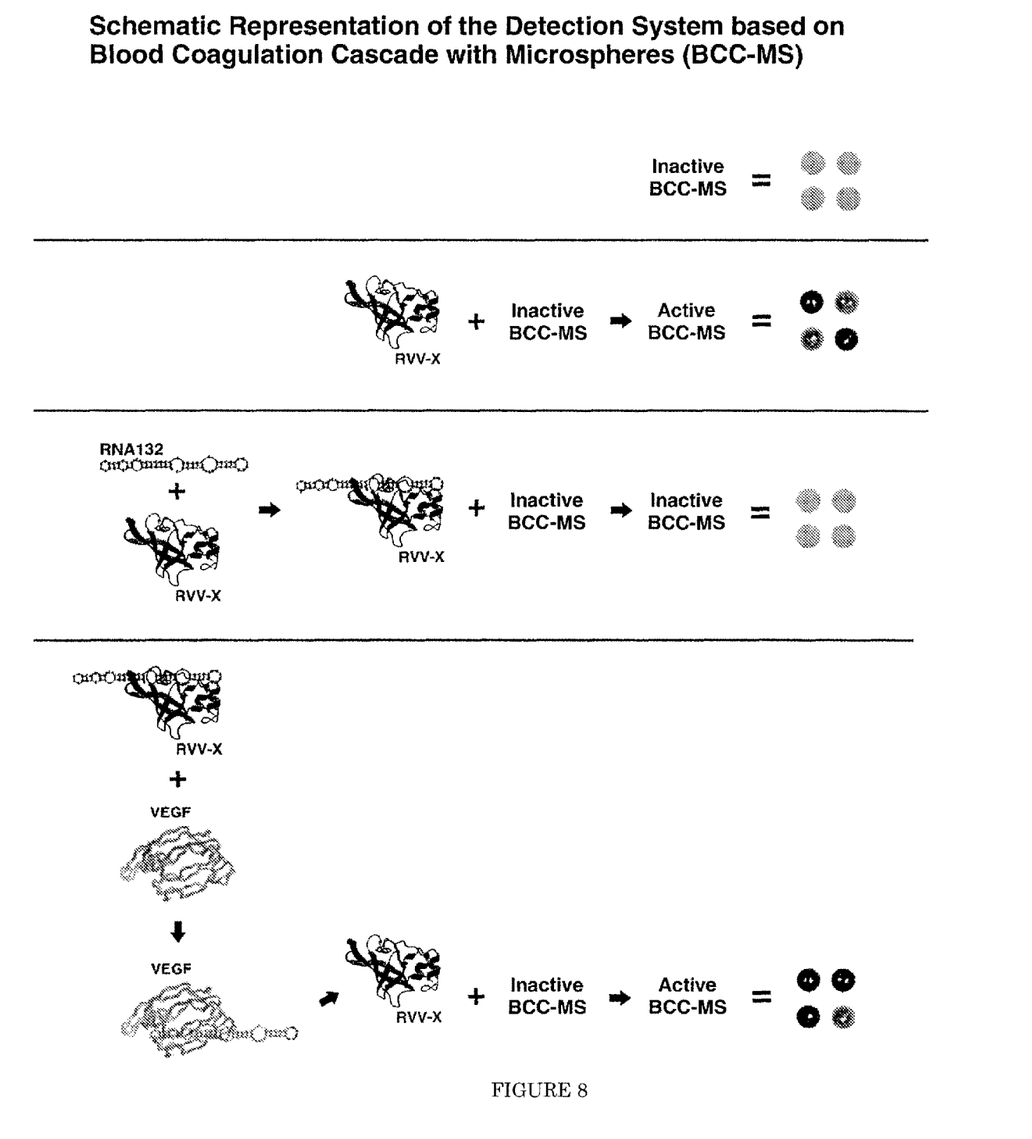
FIG. 8. Schematic representation of the detection system based on blood coagulation cascade with microspheres (BCC-MS).
Figure 9:
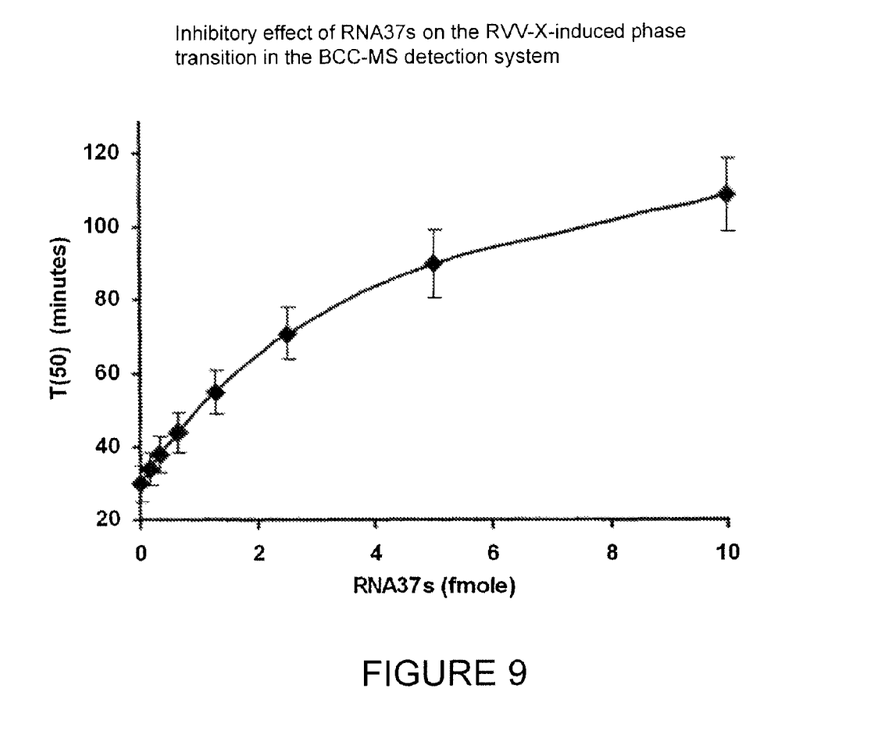
FIG. 9. Inhibitory effect of RNA37s on the RW-X-induced phase transition in the BCC-MS detection system. RNA37s was incubated with RVV-X for 15 minutes at room temperature. One hundred microliters of the BCC-MS reaction mix were dispensed into wells of a 96-well plate to which 5-10 mL of a test solution were added. After that the plate was immediately placed into a microplate reader (Genios, Tecan) and shaken for 10-30 seconds prior to OD$_{405}$ measurements at 5-10 minute intervals.
Figure 10:
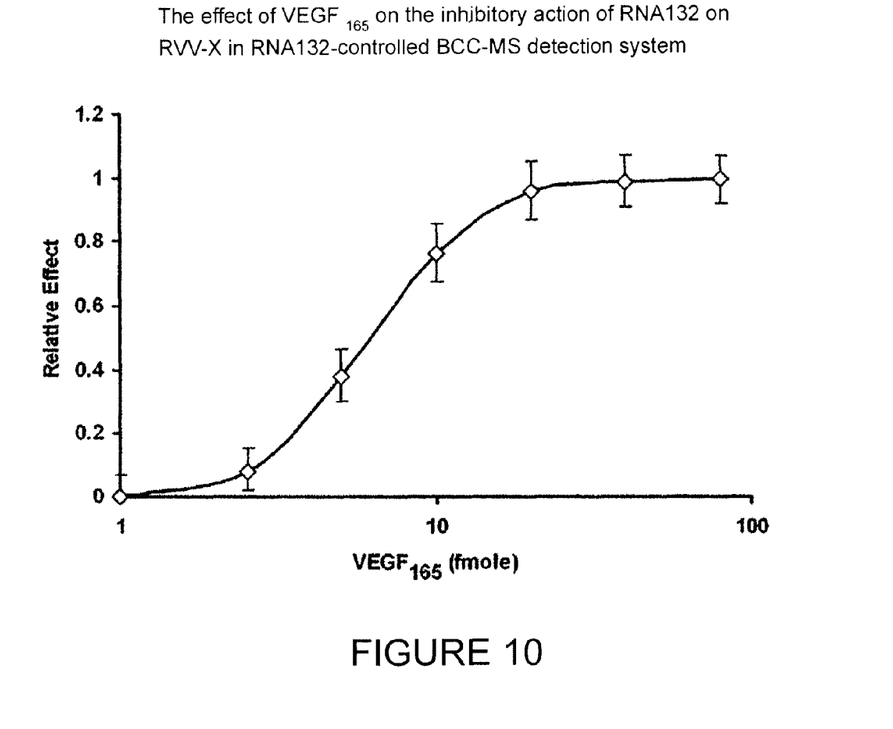
Figure 11:
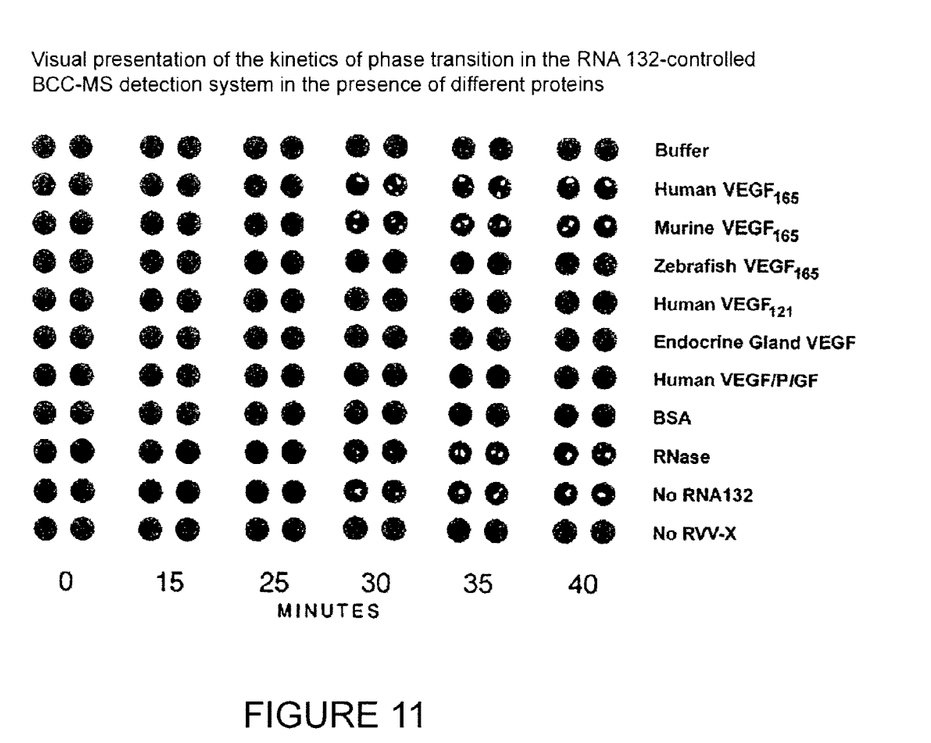
FIG. 11. Visual presentation of the kinetics of phase transition in the RNA132-controlled BCC-MS detection system in the presence of different proteins. Five femtomoles of different proteins (except for 100 fmole of RNase) were incubated with a mix of RVV-X and RNA132 for 15 minutes at RT in 5-10 uL of IC buffer, followed by the addition of the components of the BCC-MS detection system. At the indicated time points, wells of the 96-well plate were scanned on a flatbed scanner. The results are presented in duplicates.

Specificity of the BCC-MS Detection System. FIG. 5 presents the data on the specificity of the RNA132-controled BCC-MS detection system for human $VEGF_{165}$. Human $VEGF_{165}$, murine $VEGF_{165}$ and zebrafish $VEGF_{165}$ have both the same biological function and contain 165 of amino acids. Murine $VEGF_{165}$ has an 89% identity with human $VEGF_{165}$, where 147 of 165 amino acids are identical. Zebrafish $VEGF_{165}$ has about a 62% amino acid sequence identity with human $VEGF_{165}$. Human $VEGF_{121}$ is a truncated version of human $VEGF_{165}$, with 44 amino acids truncated downstream from position 110 of the polypeptide chain. Thus cysteine 137 of $VEGF_{165}$ that forms a photo-inducible cross-link to a uridine at position 14 of RNA VTt44 (22) (which corresponds to position 13 of RNA VTt44(−2) and position 18 of RNA132) is missing in $VEGF_{121}$. Human VEGF/PlGF heterodimer is a protein artificially dimerized in vitro. It consists of human $VEGF_{165}$ and Placental growth factor. The amino acid sequence of endocrine gland VEGF is unrelated to that of human VEGF. The kinetics of the clot formation were similar in the wells containing human $VEGF_{165}$ and murine $VEGF_{165}$. In both cases, the coagulation process was complete within 40 minutes. This was not surprising, since human and murine $VEGF_{165}$ are highly homologous. At the same time point (40 minutes) when the wells containing human $VEGF_{165}$ demonstrated completed coagulation, the wells containing zebrafish $VEGF_{165}$, demonstrated the onset of coagulation. It can be explained by less homology (62%) between human $VEGF_{165}$ and zebrafish $VEGF_{165}$. Meanwhile in the wells containing human $VEGF_{121}$, endocrine gland VEGF, human VEGF/PlGF, and BSA, phase transition has not been observed by that time. The results in FIG. 5 clearly demonstrate the high specificity of the detection system.

Exploration of the Possible Mechanism of the Allosteric Effect. An attempt was made to find a mechanism underlying the competition between $VEGF_{165}$ and RVV-X for the interaction with RNA132. DNA molecules complementary to different segments of RNA132 were used in the competition binding experiments of RVV-X and $VEGF_{165}$ to RNA132 (see Table 1). When a full-length DNA complement to RNA132 (DNAI) was used, no binding was observed for either of the proteins. When DNAII and DNA III compete for the RVV-X binding to the 37s domain of RNA132, predictable low levels of RVV-X binding were detected. Annealing of DNAIV to the VTt44 domain of RNA132 significantly decreases $VEGF_{165}$ binding to RNA132. When shorter DNA fragments corresponding to the VTt44 domain of RNA132 (DNAV and DNAVI) were used for the competition, the impact of competing DNA on $VEGF_{165}$ affinity for RNA132 is decreased. An unexpected inhibitory effect of DNAIV and DNAV on RVV-X binding to RNA132 was also observed. A possible explanation is that the putative stem located between positions 2-8 and 28-34 in RNA132 (FIG. 2C) is involved in the binding of both proteins. This can result in direct steric competition between the proteins. One can also speculate that the decrease of RVV-X binding in the presence of DNAIV and DNAV can be explained by assuming an alternative folding of RNA132 into a structure containing pseudoknots (FIG. 2D). Further theoretical and experimental analysis is required to more clearly describe the molecular interactions resulting in allosteric properties of RNA132.

Discussion

In this study, an allosteric RNA aptamer-based competitive homogeneous detection system with readout by the naked eye was achieved. This became possible by coupling an allosteric RNA aptamer with the biochemical signal amplification cascade, BCC-MS. The signal amplification cascade results in an eye-visible phase transition, i.e. formation of the precipitate of polystyrene microspheres bound to clotted fibrin. The allosteric aptamer contains a domain that binds to RVV-X thus inhibiting BCC. There is another domain on the allosteric aptamer, which binds to an effector molecule reversing the effect of the first domain. The latter domain of the aptamer is the only variable part of the detection system. Therefore, adjusting the detection system to a new effector molecule will involve only one molecular component—an aptamer to the effector molecule. Further, the detection system requires only 2 pipetting cycles compared with 10 in the case of ELISA, and it requires less than an hour for its completion, compared with 4.5 hours for ELISA. Most importantly, the naked eye is used as a readout instrument instead of expensive and rarely available equipment. These features make the detection system a good candidate as a platform for fieldable detection systems and make it competitive with ELISA.

While the present invention has been described herein with specific details by way of illustrations and examples, those of ordinary skill in the art will readily recognize that numerous modifications, substitutions, and alterations are possible without departing from the spirit and scope of the invention. It is intended that all of these modifications and variations be within the scope of the present invention as described and claimed herein, and that the invention be limited only by the scope of the claims which follow, and that such claims be interpreted as broadly as reasonable.

REFERENCES

The following references are cited herein. The entire disclosure of each reference is relied upon and incorporated by reference herein.

1. Osborne, S. E., Matsumura, I., and Ellington, A. D. (1997) Aptamers as therapeutic and diagnostic reagents: problems and prospects, *Curr. Opin. Chem. Biol.* 1, 5-9.

2. Jayasena, S. D. (1999) Aptamers: an emerging class of molecules that rival antibodies in diagnostics, *Clinical Chem.* 45, 1628-1650.
3. Brody, E. N., and Gold, L. (2000) Aptamers as therapeutic and diagnostic agents, *Molec. Biotechnol.* 74, 5-13.
4. Jhaveri, S. D., Kirby, R., Conrad, R., Maglott, E. J., Bowser, M., Kennedy, R. T., Glick, G., and Ellington, A. D. (2000) Designed signaling aptamers that transduce molecular recognition to changes in fluorescent intensity, *J. Am. Chem. Soc,* 122, 2469-2473.
5. Jhaveri, S., Rajendran, M., and Ellington, A. D. (2000) In vitro selection of signaling aptamers, *Nature Biotechnol.* 18, 1293-1297.
6. Hamaguchi, N., Ellington, A., and Stanton, M. (2001) Aptamer beacons for direct detection of proteins, *Anal. Biochem.* 294, 126-131.
7. Silverman, S. K. (2003) Rube Goldberg goes (ribo) nuclear? Molecular switches and sensors made of RNA, *RNA,* 9, 377-383.
8. Stojanovic, M. N., and Kolpashchikov, D. M. (2004) Modular aptameric sensors, *J. Am. Chem. Soc.* 126, 9266-9270.
9. Wang, X-L., Li, F., Su, Y-H., Sun, X, Li, X-B., Schluesener, H. J., Tang, F. and Xu, S-Q. (2004) Ultrasensitive detection of protein using an aptamer-based exonuclease protection assay, *Analytical Chem.* 76, 5605-5610.
10. Tombelli, S.; Minunni, M.; Mascini, M. (2005) Analytical applications of aptamers, *Biosensors and Bioelectronics* 20, 2424-2434.
11. Soukup, G. A. (2004) Aptamers meet allostery, *Chem. Biol.* 11, 1031-1032.
12. Wu, L., and Curran, J. F. (1999) An allosteric synthetic DNA, *Nucleic Acid Res.* 27, 1512-1516.
13. Vuyisich, M., and Beal, P. A. (2002) Controlling protein activity with ligand-regulated RNA aptamers, *Chem. Biol.* 9, 907-913.
14. Buskirk, A. R., Landrigan, A. and Liu D. R. (2004) Engineering a ligand-dependent RNA transcriptional activator, *Chem. Biol.* 11, 1157-1163.
15. Nutiu, R., and Li, Y. (2004) Structure-switching signaling aptamers: transducing molecular recognition into fluorescence signaling, *Chem. Eur. J.* 10, 1868-1876.
16. Cong, X., and Nielsen-Hamilton, M. (2005) Allosteric aptamers: Targeted reversibly attenuated probes, *Biochemistry* 44, 7945-7954.
17. Fitzwater, T. and Polisky, B. (1996) A SELEX primer, *Methods in Enzymology* 267, 275-301.
18. Pollard, J., Bell, S. D., and Ellington, A. D. (2000) Design, synthesis, and amplification of DNA pools for in vitro selection, *Current Protocols in Nucleic Acid Chemistry* 9.2.1-9.2.23.
19. Jhaveri, S. D, and Ellington, A. D. (2000) In vitro selection of RNA aptamers to a protein target by filter immobilization, *Current Protocols in Nucleic Acid Chemistry* 9.3.1-9.3.25.
20. Cox, J. C., Hayhurst, A., Hesselberth, J., Bayer, T. S., Georgiou, G., and Ellington, A. D. (2002) Automated selection of aptamers against protein targets translated in vitro: from gene to aptamer, *Nucleic Acid Res.* 30, e108, 1-14.
21. Jelinek, D., Green, L. S., Bell, C., and Janjic, N. (1994) Inhibition of receptor binding by high-affinity RNA ligands to vascular endothelial growth factor, *Biochemistry* 33, 10450-10456.
22. Ruckman, J., Green, L. S., Beeson, J., Waugh, S., Gilette, W. L., Henninger, D. D., Claesson-Welsh, L., and Janjic, N. (1998) 2'-Fluoropyrimidine RNA-based aptamers to the 165-amino acid form of vascular endothelial growth factor ($VEGF_{165}$), *J. Biol. Chem.* 273, 20556-20567.
23. Dirks, R. M., and Pierce, N. A. (2003) A partition function algorithm for nucleic acid secondary structure including pseudoknots, *J. Comput. Chem.* 24, 1664-1677.
24. Dirks, R. M., and Pierce, N. A (2004) An algorithm for computing nucleic acid base pairing probabilities including pseudoknots, *J. Comput. Chem.* 25, 1295-1304.
25. Han, K., and Byun, Y. (2003) PseudoViewer2: visualization of RNA pseudoknots of any type, *Nucleic Acid Res.* 31, 3432-3440.
26. Strachan, N. J. C., and Ogden, I. D. (2000) A sensitive microsphere coagulation ELISA for *Escherichia coli* O157:H7 using Russell's viper venom, *FEMS Microbiol. Lett.* 186, 79-84.
27. Gowda, D. C., Jackson, C. M., Hensley, P., and Davidson, E. A. (1994) Factor X activating glycoprotein of Russell's viper venom. Polypeptide composition and characterization of the carbohydrate moieties, *J. Biological Chemistry* 269, 10644-10650.
28. Doellgast, G. J., Triscott, M. X., Beard, G. A., Bottoms, J. D., Cheng, T., Roh, B. H., Roman, M. G., Hall, P. A., and Brown, J. E. (1993) Sensitive enzyme-linked Immunosorbent assay for detection of Clostridium botulinum neurotoxins A, B, and E using signal amplification via enzyme-linked coagulation assay, *J. Clin. Microbiol.* 31, 2402-2409.

29. Fish, G., Haller, J. A., Ho, A. C., Klein, M., Loewenstein, J., Martin, D., Orth, D., Rosen, R. B., Sanislo, S., Schwartz, S. D. et al. (2003) Anti-vascular endothelial growth factor therapy for subfoveal choroidal neovascularization secondary to age related macular degeneration. Phase II study results, *Ophthalmology,* 110, 979-986.

30. Dell, S. D., Denu, J. M., Dixon, J. E., and Ellington, A. D (1998) RNA molecules that bind to and inhibit the active site of tyrosine phosphatase, *J. Biol. Chem.* 273, 14309-14314.

---

What is claimed is:

1. A detection system comprising:
   a) a fusion aptamer formed by fusing a first aptamer to a second aptamer;
   b) Russell's viper venom factor X activator (RVV-X); and
   c) a biochemical signal amplification subsystem comprising blood coagulation components and a signaling agent,
   wherein said first aptamer is one specific for RVV-X, said second aptamer is one specific for a target molecule to be detected, and said signaling agent is one capable of interacting with the product of blood coagulation cascade reaction to give a visual signal readable by the naked eye.

2. The detection system according to claim 1, wherein the first aptamer is one having a sequence according to SEQ ID No: 1.

3. The detection system according to claim 1, wherein said signaling agent is a polystyrene microsphere.

4. The detection system according to claim 1, wherein the second aptamer is one specific for human vascular endothelial growth factor ($VEGF_{165}$) or a protein tyrosine phosphatase from *Yersinia enterocolitica*.

5. The detection system according to claim 1, wherein said fusion aptamer is one having a sequence according to SEQ ID No: 5.

6. A fusion aptamer formed by fusing a first aptamer specific for RVV-X and a second aptamer specific for a target molecule.

7. The fusion aptamer of claim 6, wherein said first aptamer is one having a sequence according to SEQ ID No: 1.

8. The fusion aptamer of claim 6, wherein said fusion aptamer having a sequence according to SEQ ID No: 3.

9. The fusion aptamer of claim 6, wherein said fusion aptamer having a sequence according to SEQ ID No: 5.

10. A method for detecting a target molecule in a sample, comprising:

contacting the sample with RVV-X, a fusion aptamer, blood coagulation components and a signaling agent, wherein said fusion aptamer is formed by fusing a first aptamer specific for RVV-X and a second aptamer specific for said target molecule, said signaling agent is one capable of interacting with the product of blood coagulation cascade reaction to give a visual signal readable by the naked eye, and whereby presence of the target molecule in the sample initiates a blood coagulation cascade reaction to give a visual signal.

11. The method of claim 10, wherein said RVV-X, fusion aptamer, blood coagulation components, and signaling agent are pre-mixed together prior to contacting the sample.

12. The method of claim 10, wherein said sample, blood coagulation components and signaling agent are brought in contact first before a mixture of RVV-X and the fusion aptamer are added.

13. The method of claim 10, wherein said first aptamer specific for RVV-X is one having a sequence according to SEQ ID No: 1.

14. The method of claim 10, wherein said fusion aptamer is one having a sequence according to SEQ ID No: 3 or SEQ ID No: 5.

15. The method of claim 10, wherein said target molecule is one selected from $VEGF_{165}$ or a protein tyrosin phosphatase.

16. The method of claim 10, wherein said signaling agent is a polystyrene microsphere.

* * * * *